(12) United States Patent
Dubat et al.

(10) Patent No.: US 9,067,210 B2
(45) Date of Patent: Jun. 30, 2015

(54) METHOD AND DEVICE HAVING A SIMPLIFIED CONSTRUCTIONS FOR THE REFERENCE GRINDING OF WHEAT

(75) Inventors: Arnaud Dubat, Fourqueux (FR); Sonia Geoffroy, Brie Comte Robert (FR); Joël Abecassis, Les Cres (FR); Marc Chaurand, Monteferrier sur Lez (FR); Robert Pujol, Teyran (FR); Christine Bar-L'Helgouac'h, Paris (FR)

(73) Assignees: CHOPIN TECHNOLOGIES, Villeneuve-la-Garenne (FR); INRA (INSTITUT NATIONAL DE LA RECHERCHE AGRONOMIQUE), Paris (FR); ARVALIS (INSTITUT DU VEGETAL), Paris (FR)

( * ) Notice: Subject to any disclaimer, the term of this patent is extended or adjusted under 35 U.S.C. 154(b) by 333 days.

(21) Appl. No.: 13/510,706

(22) PCT Filed: Nov. 19, 2010

(86) PCT No.: PCT/FR2010/000773
§ 371 (c)(1),
(2), (4) Date: Jun. 27, 2012

(87) PCT Pub. No.: WO2011/061420
PCT Pub. Date: May 26, 2011

(65) Prior Publication Data
US 2012/0267457 A1      Oct. 25, 2012

(30) Foreign Application Priority Data

Nov. 20, 2009   (FR) ..................................... 09 05572

(51) Int. Cl.
*B02B 5/00*        (2006.01)
*B02C 9/04*        (2006.01)
*B02C 9/00*        (2006.01)
*G01N 15/02*       (2006.01)
*B02C 4/06*        (2006.01)

(52) U.S. Cl.
CPC ... *B02C 9/04* (2013.01); *B02C 9/00* (2013.01); *G01N 15/02* (2013.01); *B02C 4/06* (2013.01)

(58) Field of Classification Search
CPC .............. B02C 9/00; B02C 9/04; B02C 4/06; A47J 42/38; B02B 3/04; B02B 1/00; B02B 5/02; B02B 5/00; G01N 5/02; A23L 1/172; A21D 2/265
USPC .......................... 241/6–13; 426/622, 518–19
See application file for complete search history.

(56) References Cited

U.S. PATENT DOCUMENTS 2,392,365 A * 1/1946 Carter ............................... 241/7
4,133,899 A * 1/1979 Wolffing et al. ............... 426/507
(Continued)

FOREIGN PATENT DOCUMENTS

| | | |
|---|---|---|
| CH | 528 302 A | 9/1972 |
| EP | 0 339 577 A2 | 11/1989 |
| EP | 0 433 498 A1 | 6/1991 |

OTHER PUBLICATIONS

International Search Report, dated Apr. 4, 2011, from corresponding PCT application.

*Primary Examiner* — Faye Francis
*Assistant Examiner* — Onekki Jolly
(74) *Attorney, Agent, or Firm* — Young & Thompson

(57) ABSTRACT

A process for simplified production of a reference milling for determining the milling quality of wheat, includes: a first crushing of a wheat sample; a first sieving of the crushed product into three distinct levels of particle size; a second crushing of oversize particles resulting from the first crushing; a second sieving of the oversize particles thus crushed; a mixing of coarse semolina resulting from the sievings; a third crushing of the mixture of the coarse semolina; a third sieving of the mixture of the coarse semolina thus crushed into two distinct levels of particle size; a mixing of fine semolina resulting from each of the three sievings; a fourth crushing of the mixture of fine semolina; a fourth sieving of the mixture of the fine semolina thus crushed into a single level of particle size; a mixing of the flours resulting from sievings, the mixture constituting the desired milling.

20 Claims, 1 Drawing Sheet

(56) References Cited

U.S. PATENT DOCUMENTS

| | | | |
|---|---|---|---|
| 4,986,997 A * | 1/1991 | Posner et al. ............ 426/622 |
| 5,114,079 A * | 5/1992 | Curran ............... 241/3 |
| 5,115,984 A * | 5/1992 | Satake ............... 241/7 |
| 5,192,028 A * | 3/1993 | Curran ............... 241/3 |

* cited by examiner

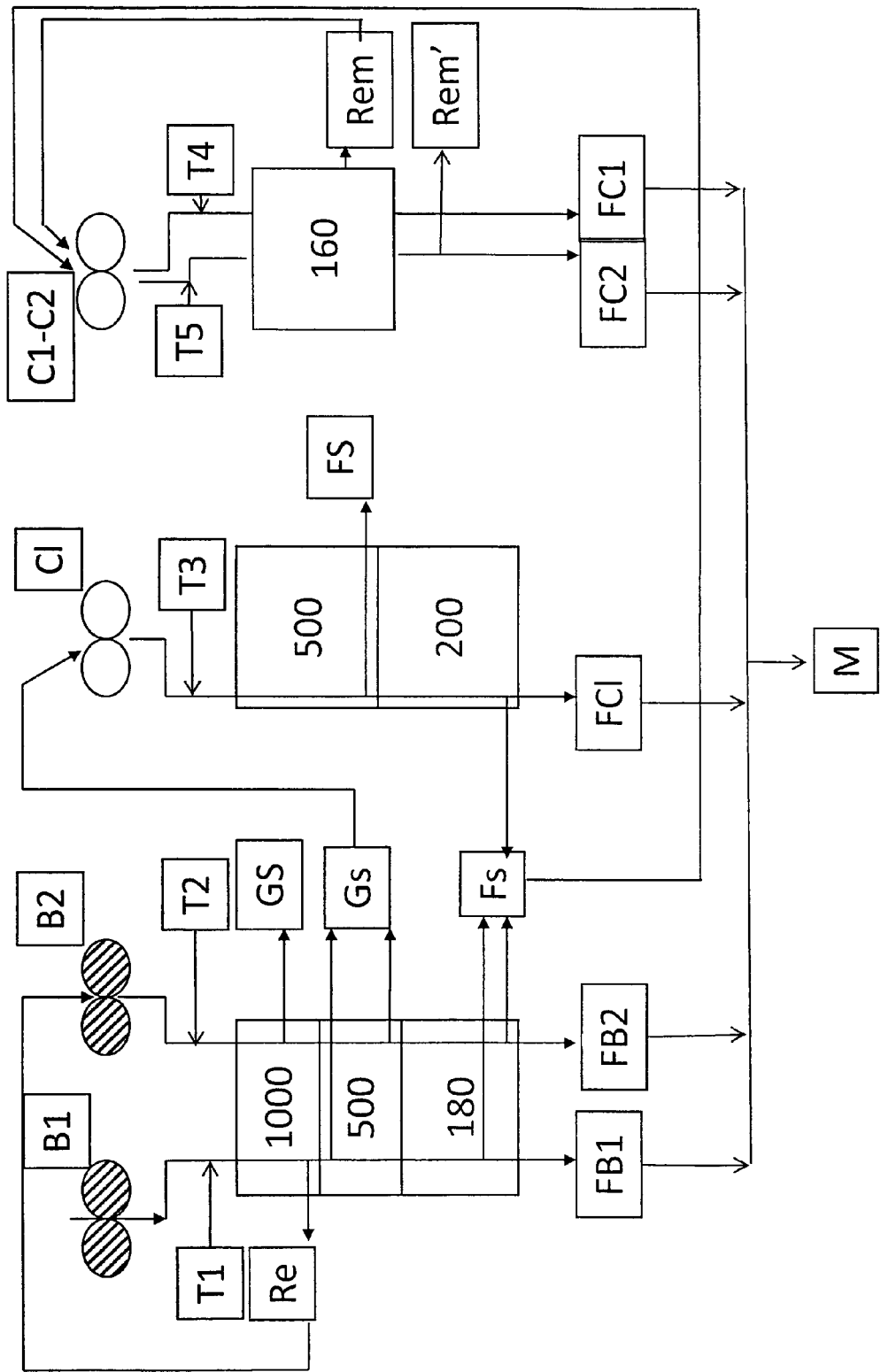

METHOD AND DEVICE HAVING A SIMPLIFIED CONSTRUCTIONS FOR THE REFERENCE GRINDING OF WHEAT

The invention relates to a process for simplified production of reference milling for the purpose of determining the milling quality of wheat.

The invention also relates to a device for implementing the process.

Document U.S. Pat. No. 4,986,997 describes a sequential process for processing wheat as an adjunct to conventional milling that enables the recovery of substantial quantities of wheat embryo and scutellum, to thus increase the yield of first quality germ while enhancing suitability for storage of the flour obtained because of the elimination of the fractions of the germ oil. The process involves the initial tempering of the wheat, followed by impact scouring designed to remove the embryo intact; then, the wheat freed of its embryo is subjected to a second tempering stage prior to milling. The crushing system of the mill is appropriately modified by a judicious selection of the milling gap so as to permit recovery of the intact scutellum, especially from hard red winter wheat.

Document CH528302 describes a laboratory grain crusher that comprises streams of grain and crushed elements connected by pipes with, below the latter, separators installed to sort the crushed products into fractions and containers that collect the flour, as well as pipes to evacuate the bran from the containers, characterized by the fact that the evacuation pipes are connected to the same streams of grain and crushed elements for evacuating the bran using additional bypass pipes provided with separator valves to divide the stream of crushed products, in which case the containers that collect the flour are placed on a scale provided with a sensor that reacts when the prescribed degree of crushing per weight is attained and that sends a command to stop the drive of the crusher.

Document U.S. Pat. No. 4,133,899 describes a wheat crushing process designed to produce a large proportion of coarse farina in which the wheat, having undergone a double tempering passes through a series of four identical sets of coarsely and deeply grooved, fast-acting crushing rollers. The product at the output of each roller is separated into a range of sizes. The substantially too coarse particles coming from each set of crushing rollers are directed towards the subsequent set of crushing rollers of the series. The slightly too coarse particles are directed towards grooved rollers to reduce their size slightly and to remove the bran coat. The particles that have the proper size are air purified to remove the bran particles and too coarse bran particles undergo additional crushing operations designed to separate any endosperm particles from them.

Document EP0433498 relates to a device for crushing granular material into crushed particles that comprises a pair of mounted rotary rollers placed opposite one another. At least one of the rollers can move towards the other. A gap-adjusting unit is connected to at least one roller and designed to move it towards or away from the other roller to adjust the gap between them so as to adjust the degree of crushing of the crushed particles. The gap-adjusting unit is operational in response to an output signal coming from the measuring unit.

Document EP 0339 577 relates to a process for milling grains that comprises stages of grain polishing, crushing, and sifting, repeated in an alternating fashion, of the polished grains, of recovery of the milling, and a stage for moistening crushed grains during the crushing and sifting stage.

To achieve an industrial milling of wheat, numerous operations are performed, in particular crushing and sieving operations on large quantities.

With the intention of predicting the milling quality of the wheat and, in particular, its milling yield starting from the milling of a small quantity of grain, an effort has been made to limit and simplify at best the necessary operations so as to make such prediction possible with simplified equipment of the laboratory type. However, the flour obtained must, of course, have characteristics comparable to those of a flour obtained in an industrial mill.

After numerous studies and tests, the inventors were able to develop a process of simplified production for such a milling that is particularly noteworthy in that it consists in performing:

a first crushing of a wheat sample;

a first sieving of the product thus crushed into three distinct levels of particle size, producing four products referred to below according to a decreasing particle size: oversize particles, coarse semolina, fine semolina, and first-crushing flour;

a second crushing of the oversize particles resulting from the first crushing;

a second sieving of the oversize particles thus crushed, similar to the first sieving, producing four sorted products referred to below according to a decreasing particle size: coarse bran, coarse semolina, fine semolina, and second-crushing flour;

a mixing of the coarse semolina resulting from the sievings that follow the first and second crushings respectively;

a third crushing of the mixture of the coarse semolina previously obtained;

a third sieving of the mixture of the coarse semolina thus crushed into two distinct levels of particle size, producing three sorted products referred to below according to a decreasing particle size: fine bran, fine semolina, and third-crushing flour;

a mixing of the fine semolina resulting from each of the three sievings that follow the three above-mentioned crushings;

a fourth crushing of the mixture of the fine semolina previously obtained;

a fourth sieving of the mixture of the fine semolina thus crushed into a single level of particle size producing two sorted products referred to below according to a decreasing particle size: sharps and fourth-crushing flour;

A mixing of the flours resulting from the sievings that follow the four crushings, said mixture constituting the desired milling.

Preferably, there is performed a fifth crushing of the sharps resulting from the sieving that follows the fourth crushing and a fifth sieving of the sharps thus crushed into a single level of particle size producing two sorted products referred to below according to a decreasing particle size: sharps bis and fifth-crushing flour, this flour being added to the mixture of the other flours to constitute the desired milling.

According to an embodiment, the second sieving that follows the second crushing is performed using the same sieving system as that used for the first sieving that follows the first crushing and advantageously, the fifth crushing and the fifth sieving are obtained by a repetition of the fourth crushing and the fourth sieving respectively, the fifth-crushing flour being added to the fourth-crushing flour.

According to an embodiment, the three levels of particle size of the sievings that follow the first and second crushings are approximately 200, 500, and 1000 microns respectively, the two levels of particle size from the sieving that follows the third crushing are approximately 200 and 500 microns respectively and the particle size of the sievings that follow the fourth and fifth crushings is approximately 160 microns.

Preferably, the feed rates for the crushings are between 3 g/s and 8 g/s respectively for the first two and between 1 g/s and 4 g/s for the subsequent ones.

The first and second crushings are, for example, each performed using two grooved rollers of the back-to-back type, whereas the third, fourth, and optionally a fifth crushing, generally referred to as course and fine reduction respectively, are performed each using two smooth rollers.

According to an embodiment, the speeds of the fast rollers for each crushing are, in the order of the operations, approximately 500 and 1000 rpm for the first two crushings respectively and 600 rpm for the subsequent ones, the differential coefficients between the speeds of the fast rollers and the slow rollers for each crushing are, in the order of the operations, approximately 2.5 and 3.5 for the first two crushings respectively and 1.5 for the subsequent ones, whereas the roller gaps for each crushing are, in the order of the operations, approximately 0.70 mm and 0.10 mm for the first two crushings respectively and 0.03 mm for the subsequent ones.

The invention also relates to a device for implementing the above-mentioned process, which is particularly noteworthy in that it comprises four or five successive crushers, each followed by a sieving system having only three levels of particle size for the first two crushers, only two levels for the third crusher and a single level for the subsequent crusher or crushers respectively.

According to an embodiment, the sieving system of the first and second crushers is shared. For example, and advantageously, the device comprises only four crushers, each followed by a sieving system, some of which can be shared, the fourth crusher and the fourth sieving system being arranged to ensure the role of a fifth crusher and of a fifth sieving system respectively.

Lastly and preferably, the crushers are each provided with two rollers, whereas the rollers of the first two crushers are grooved and of the back-to-back type and those of the two or three other crushers are smooth.

The invention will be well understood from reading the description that will follow and that refers to the attached diagram (single FIGURE).

A process and at the same time a device according to the invention are diagrammatically depicted.

The process and the device described below are provided by way of example of an embodiment. Consequently, the values indicated must therefore not be considered as limiting the invention, even if they appear preferable.

To obtain the desired reference milling, first of all a first crushing B1 of a wheat sample using a crusher is performed and the product thus crushed is then sieved as depicted in the diagram, according to a first sieving T1 which, as the diagram shows, is performed into three levels of particle size, here, in particular, 200, 500, and 1000 microns respectively.

Preferably, the crusher for the first crushing B1, like all the other crushers that will be discussed below, comprises two rollers.

The sieving T1, like the other sievings that will be discussed below, is advantageously obtained using systems that comprise stacks of sieves and that use centrifuging.

Owing to the sieving T1 having three levels, four sorted products referred to below are obtained: oversize particles Re having a particle size greater than 1000 microns, coarse semolina Gs having a particle size less than 1000 microns and greater than 500 microns, fine semolina Fs having a particle size between 200 microns and 500 microns and first-crushing flour FB1 having a particle size less than 200 microns.

The oversize particles Re then undergo a second crushing B2 and are again sifted through a sieving T2, which again uses exactly the same levels of particle size as the first sieving T1 of 1000 microns, 500 microns, and 200 microns, to likewise obtain four sorted products referred to below respectively and according to a decreasing order of particle size: coarse bran GS, coarse semolina Gs, fine semolina Fs and second-crushing flour FB2, the latter therefore having a particle size less than 200 microns.

As the diagram further shows, the second sieving T2 is performed with the same system as that used for the first sieving T1, but it could, of course, be totally separate.

Following the sievings T1 and T2, the coarse semolina Gs and the fine semolina Fs resulting from each of said sievings are mixed.

The coarse semolina Gs thus recovered undergoes a third crushing Cl, generally referred to as coarse reduction, and the products thus crushed undergo a third sieving T3 into two levels of particle size, here of 500 microns and 200 microns, obtaining three sorted products referred to respectively: fine bran having a particle size greater than 500 microns, fine semolina with a particle size between 200 microns and 500 microns, and a third-crushing flour FCl with a particle size less than 200 microns.

The fine semolina Fs resulting from this third sieving T3 is then mixed with those obtained from the two other previous sievings T1 and T2 to have them undergo a fourth crushing C1, generally referred to as fine reduction.

The fine semolina Fs thus crushed during the fourth crushing C1 undergoes a sieving T4 into a single level of particle size of 160 microns producing two sorted products referred to below as sharps Rem with a particle size greater than 160 microns and fourth-crushing flour FC1 with a particle size less than 160 microns.

In the depicted diagram, the sharps Rem undergo a fifth crushing C2, here using the same crusher as previously, whereas the sharps Rem thus crushed undergo a fifth sieving T5 using the same sieving system as the preceding one.

In this way, two sorted products are obtained, namely sharps bis Rem' with a particle size greater than 160 microns and a fifth-crushing flour FC2 with a particle size less than 160 microns.

However, for the fifth crushing C2 and the fifth sieving T5, it is of course conceivable to perform them with a crusher and sieving system that are separate and different from those used for the fourth crushing C1 and the fourth sieving T4.

Also, similarly, when the fifth crushing C2 of the sharps Rem and fifth sieving T5 of the product thus crushed are recommended, the process could be stopped at the fourth crushing and fourth sieving.

It is sufficient then to mix the flours FB1, FB2, FCl, FC1, and FC2 resulting from the five crushings and sievings to obtain the desired milling M.

According to an embodiment, the feed rates for the crushings B1 and B2 are, for example, between 3 g/s and 8 g/s and they are between 1 g/s and 4 g/s for the crushings Cl, C1, and C2 respectively.

If crushers advantageously having two rollers are used for the crushings B1, B2, Cl, (C1, C2), as already stated, the rollers for the crushings B1, B2 are advantageously grooved and back-to-back, whereas the rollers for the other crushings Cl, C1, C2 are preferably smooth.

Moreover, the speeds of the fast rollers for each crushing are 500 rpm for the crushing B1, 1000 rpm for the crushing B2 and 600 rpm for the crushings Cl, (C1, C2) respectively.

The differential coefficients between the speeds of the fast rollers and the slow rollers for each crushing are approximately 2.5 for crushing B1, 3.5 for crushing B2, and 1.5 for crushings Cl, (C1, C2) respectively.

Lastly, the roller gaps for each crushing are, for example, 0.70 mm for crushing B1, 0.10 mm for crushing B2, and 0.03 mm for crushings Cl, (C1, C2) respectively.

The device according to the invention for implementing the process was explicitly described at the same time as the process and comprises four or five crushers and three, four, or five sieving systems (certain crushers and/or sieving systems can be shared as specified above).

If depiction of the various means used is desired, it is sufficient to assign the references designating the crushings B1, B2, Cl, C1-C2 and the sievings T1-T5 of the process to the crushers and sieving systems of the device respectively.

The invention claimed is:

1. A process for simplified production of a reference milling for determining a milling quality of wheat, comprising the steps of:
    a first crushing (B1) of a wheat sample into a crushed product;
    a first sieving (T1) of the crushed product into three distinct levels of particle size to produce four first products: oversize particles (Re), first-crushing coarse semolina, first-crushing fine semolina, and first-crushing flour (FB1);
    a second crushing (B2) of the oversize particles (Re) to produce crushed oversize particles;
    a second sieving (T2) of the crushed oversize particles into three distinct levels of particle size to produce four sorted second products: coarse bran (GS), second-crushing coarse semolina (Gs), second-crushing fine semolina and second-crushing flour (FB2);
    a mixing of the first-crushing coarse semolina and the second-crushing coarse semolina to produce a mixture of coarse semolina;
    a third crushing (C1) of the mixture of coarse semolina to produce a crushed mixture of coarse semolina;
    a third sieving (T3) of the crushed mixture of coarse semolina into two distinct levels of particle size to produce three sorted third products: fine bran (FS), third-crushing fine semolina and third-crushing flour (FC1);
    a mixing of the first-crushing fine semolina, the second-crushing fine semolina, and the third-crushing fine semolina to produce a mixture of fine semolina;
    a fourth crushing (C1) of the mixture of fine semolina to produce a crushed mixture of fine semolina;
    a fourth sieving (T4) of the mixture of fine semolina (Fs) into a single level of particle size to produce two sorted fourth products: sharps (Rem) and fourth-crushing flour (FC1); and
    a mixing of the first-crushing flour (FB1), the second-crushing flour (FB2), the third-crushing flour (FB3), and the fourth-crushing flour (FB4) to produce a milling (M).

2. The process according to claim 1, further comprising:
    a fifth crushing (C2) of the sharps (Rem) to produce crushed sharps; and
    a fifth sieving (T5) of the crushed sharps into a single level of particle size to produce two sorted products: sharps bis (Rem') and fifth-crushing flour (FC2), wherein the fifth-crushing flour (FC2) is mixed together with the first-crushing flour (FB1), the second-crushing flour (FB2), the third-crushing flour (FB3), and the fourth-crushing flour (FB4) of the milling (M).

3. The process according to claim 1, wherein the second sieving (T2) and the first sieving (T1) are both performed using a same sieving system.

4. The process according to claim 2, wherein the fifth crushing (C2) and the fifth sieving (T5) are obtained by a repetition of the fourth crushing (C1) and the fourth sieving (T4) respectively, the fifth-crushing flour (FC2) being added to the fourth-crushing (C1) flour (FC1).

5. The process according to claim 1, wherein, for the first sieving and the second sieving, the three levels of particle size are approximately 200, 500 and 1000 microns, respectively.

6. The process according to claim 1, wherein, for the third sieving, the two levels of particle size are approximately 200 and 500 microns, respectively.

7. The process according to claim 2, wherein the particle size of the fourth sieving (T4) and the fifth sieving (T5) is approximately 160 microns.

8. The process according to claim 2, wherein the feed rates to the first crushing (B1) and the second crushing (B2) are between 3 g/s and 8 g/s, and the feed rates to the third crushing, the fourth crushing, and the fifth crushing are between 1 g/s and 4 g/s.

9. The process according to claim 1,
    wherein the first and second crushings (B1, B2) are each performed using two grooved rollers, and
    wherein the third and fourth crushings are each performed using two smooth rollers.

10. The process according to claim 9,
    wherein fast rollers of the first and second crushings operate at approximately 500 and 1000 RPM, respectively, and
    wherein fast rollers of the third and fourth crushings operate at approximately 600 RPM.

11. The process according to claim 9,
    wherein a differential coefficient between speeds of the fast rollers of the first crushing and slow rollers of the first crushing is approximately 2.5,
    wherein a differential coefficient between speeds of the fast rollers of the second crushing and slow rollers of the second crushing is approximately 3.5, and
    wherein a differential coefficient between speeds of the fast rollers and slow rollers of the third crushing and the fourth crushing is 1.5.

12. The process according to claim 9,
    wherein roller gaps for the first crushing and the second crushing are approximately 0.70 mm and 0.10 mm, respectively, and
    wherein a roller gap for the third crushing and the fourth crushing is 0.03 mm.

13. A device for grinding wheat, comprising:
    four successive crushers, each of said crushers in communication with a sieving system,
    wherein first and second crushers (B1, B2) produce only three levels of particle size, a third crusher (Cl) following the second crusher (B2) produces only two levels of particle size, and a fourth crusher following the third crusher (Cl) produces a single level of particle size, and
    wherein the device is configured to operate such that
        the first crusher performs a first crushing (B1) of a wheat sample into a crushed product,
        the sieving system performs a first sieving (T1) of the crushed product into three distinct levels of particle size to produce four first products: oversize particles (Re), first-crushing coarse semolina, first-crushing fine semolina, and first-crushing flour (FB1),
        the second crusher performs a second crushing (B2) of the oversize particles (Re) to produce crushed oversize particles,
        the sieving system performs a second sieving (T2) of the crushed oversize particles into three distinct levels of particle size to produce four sorted second products:

coarse bran (GS), second-crushing coarse semolina (Gs), second-crushing fine semolina and second-crushing flour (FB2), the third crusher performs a third crushing (Cl) of a mixture of the first-crushing coarse semolina and the second-crushing coarse semolina to produce a crushed mixture of coarse semolina, the sieving system performs a third sieving (T3) of the crushed mixture of coarse semolina into two distinct levels of particle size to produce three sorted third products: fine bran (FS), third-crushing fine semolina and third-crushing flour (FC1), a fourth crusher performs a fourth crushing (C1) of a mixture of the first-crushing fine semolina, the second-crushing fine semolina, and the third-crushing fine semolina to produce a crushed mixture of fine semolina, and the sieving system performs a fourth sieving (T4) of the mixture of fine semolina (Fs) into a single level of particle size to produce two sorted fourth products: sharps (Rem) and fourth-crushing flour (FC1), a mixture of the first-crushing flour (FB1), the second-crushing flour (FB2), the third-crushing flour (FB3), and the fourth-crushing flour (FB4) producing a final milling product (M).

14. The device according to claim 13, wherein a portion of the sieving system operates with both the first crusher (B1) and the second crusher (B2).

15. The device according to claim 13, comprising:
only the first, second, third, and fourth crushers, each in communication with the sieving system,
wherein the fourth crusher (C1) is configured to perform, after the fourth crushing, a subsequent fifth crushing of the sharps (Rem) produced by the fourth crushing to produce crushed sharps, and the sieving system is arranged to perform a fifth sieving (T5) of the crushed sharps into a single level of particle size to produce two sorted products: sharps bis (Rem') and fifth-crushing flour (FC2), and wherein the final milling product (M) includes the fifth-crushing flour (FC2).

16. The device according to claim 13,
wherein the first, second, third, and fourth crushers are each provided with two rollers,
rollers of the first and second crushers (B1, B2) being grooved and, and rollers of the third and fourth crushers (Cl, C1, C2) being smooth.

17. The process according to claim 2, wherein the second sieving (T2) and the first sieving (T1) are both performed using a same sieving system.

18. The process according to claim 3, wherein the fifth crushing (C2) and the fifth sieving (T5) are obtained by a repetition the fourth crushing (C1) and of the fourth sieving (T4) respectively, the fifth-crushing flour (FC2) being added to the fourth-crushing (C1) flour (FC1).

19. The process according to claim 10,
wherein differential coefficients between speeds of the fast rollers and slow rollers for the first crushing and the second crushing are approximately 2.5 and 3.5, respectively, and
wherein a differential coefficient between speeds of the fast rollers and slow rollers of the third crushing and the fourth crushing is 1.5.

20. The device according to claim 14, comprising:
only the first, second, third, and fourth crushers, each in communication with the sieving system,
wherein the fourth crusher (C1) is configured to perform, after the fourth crushing, a subsequent fifth crushing of the sharps (Rem) produced by the fourth crushing to produce crushed sharps, and the sieving system is arranged to perform a fifth sieving (T5) of the crushed sharps into a single level of particle size to produce two sorted products: sharps bis (Rem') and fifth-crushing flour (FC2), and
wherein the final milling product (M) includes the fifth-crushing flour (FC2).

* * * * *